(12) United States Patent
Seedhom (10) Patent No.: US 6,193,754 B1
(45) Date of Patent: Feb. 27, 2001

(54) ATTACHMENT DEVICE FOR USE IN THE IMPLANTATION OF PROSTHETIC LIGAMENT

(75) Inventor: Bahaa Botros Seedhom, Leeds (GB)

(73) Assignee: Neoligaments Limited, Leeds (GB)

( * ) Notice: Subject to any disclaimer, the term of this patent is extended or adjusted under 35 U.S.C. 154(b) by 0 days.

(21) Appl. No.: 09/269,329

(22) PCT Filed: Sep. 26, 1997

(86) PCT No.: PCT/GB97/02612

§ 371 Date: May 21, 1999

§ 102(e) Date: May 21, 1999

(87) PCT Pub. No.: WO98/12991

PCT Pub. Date: Apr. 2, 1998

(30) Foreign Application Priority Data

Sep. 26, 1996 (GB) .................................................. 9620046

(51) Int. Cl.[7] ...................................................... A61F 2/08
(52) U.S. Cl. .......................................................... 623/13.11
(58) Field of Search ........................... 623/13.11, 13.14; 606/72

(56) References Cited

U.S. PATENT DOCUMENTS

| 4,823,794 | 4/1989 | Pierce ..................................... 128/335 |
| 5,306,301 | 4/1994 | Graf et al. ............................... 623/13 |
| 5,571,184 | * 11/1996 | Desatnick ............................... 606/72 |
| 5,769,894 | * 6/1998 | Ferragamo ............................ 623/13.14 |

FOREIGN PATENT DOCUMENTS

| 296 07 352 U | 1/1996 | (DE) . |
| WO 96 29029 | 9/1996 | (WO) . |

* cited by examiner

Primary Examiner—David J Isabella
(74) Attorney, Agent, or Firm—Workman, Nydegger & Seeley (57) ABSTRACT

An attachment device includes an elongate guide element which is manipulatable between a pulling position in which its longitudinal axis extends generally parallel to the pulling direction and an anchoring position in which its longitudinal axis extends transversely to the pulling direction. A connecting loop of flexible and implantable material is connected, or connectable, at one end to the guide element and at its other end is connectable to one end of the prosthetic ligament to be implanted. The loop is assembled from a fibre bundle of twisted yarn. Connecting apparatus are formed in the guide elements which permit the loop to be connected thereto. Connector structure is provided on the guide elements to permit lines to be connected to the element in order to pull the guide element, and a trailing implantation system connected thereto, through bone tunnels with the guide element orientated so that its longitudinal axis extends generally parallel to the pulling direction until the element emerges from the mount at one end of one of the tunnels, whereby the guide element is manipulatable by the lines so as to overlie the mouth and thereby anchor one end of the implantation system.

21 Claims, 5 Drawing Sheets

ATTACHMENT DEVICE FOR USE IN THE IMPLANTATION OF PROSTHETIC LIGAMENT

BACKGROUND OF THE INVENTION

1. Field of the Invention

This invention is concerned generally with the implantation of a prosthetic ligament, and in particular with providing an improved attachment device for use in guiding a prosthetic ligament to a required position within a bone joint, and to anchor one end of the ligament.

2. Present State of the Art

In the implantation of a prosthetic ligament in a bone joint e.g. the knee joint between tibial and femoral components, it is usual to drill tunnels through the bones, and to pull the prosthetic ligament through the tunnels until a required position is reached within the joint, followed by suitable anchoring of the ligament against linear movement in either direction. The anchoring may involve use of bone staples or other intrusive fixations, which attach tensile elements (connected to each end of the ligament) to suitable bone sites adjacent to the mouths of the bone tunnels.

Prosthetic ligaments can be made of synthetic material, provided that it is of suitable implantable nature, and which may be woven, or autogenous tissue harvested from the patient can be used.

One more recent endoscopic technique which has been developed in ACL reconstruction (anterior cruciate ligament reconstruction), involves use of an attachment device which serves both to guide the implantation of the ligament, and to secure one end of the ligament against axial movement in one direction, but the attachment device is of such a construction that it does not need to anchor itself in position by physical intrusion into the bone.

The attachment device used in the technique provides easy guidance of the ligament, by forming the lead element of a trailing implantation system, and which passes through the usual drilled-out bone tunnels, and then upon exiting of the lead element from an upper mouth of one of the tunnels i.e. when it projects upwardly out of the femoral component, a simple manipulation of the device causes it to overlie the mouth of the tunnel, and thereby provide tensile restraint for the ligament end of the now implanted ligament to which it is attached.

The attachment device therefore is capable of being manipulated between a pulling position, in which it has reduced lateral extent relative to the pulling direction, and to an anchoring position in which it has maximum lateral extent relative to the pulling direction.

This known attachment device comprises a small metal bar which is about 12 mm in length, 4 mm wide and 1.5 mm in thickness, and has a row of four circular holes extending through it, of which the two outermost holes serve for attachment of two separate pulling sutures, and the inner pair of holes serve to attach the metal bar to the trailing ligament via a further set of sutures. The set of pulling sutures is taken first through the lower end of the lowermost bone tunnel in the tibial component and then passes upwardly through the bone tunnel in the femoral component, and pulls the trailing ligament system behind it. In practice only one of the sutures has tension applied to it sufficient to pull the metal bar behind it with the bar manipulating itself to take-up the pulling position of reduced lateral projection, and to be pulled lengthwise through the tunnels. Since the bar orientates itself so that its longitudinal axis aligns itself with the pulling direction, the diameter of the final passage drilled through the femoral component can be reduced, compared with the larger diameter of the tunnel which is formed so as to receive the implanted ligament. This final passage therefore can have a diameter of slightly more only than the maximum transverse dimension of the bar (4 mm). Upon exiting from the femoral component, the other pulling suture is then operated so as to manipulate the bar to take-up a transverse position in which its longitudinal axis is generally perpendicular to the passage whereby it can overlie the exit mouth of the small diameter passage. Downward tension applied to the trailing assembly attached to the bar then anchors the attachment bar in position in a non-intrusive manner with respect to the surrounding bone.

The trailing assembly which follows the pulling-through of the attachment bar usually comprises (a) further sutures which are taken through the central pair of holes in the bar, and then connected together to complete the formation of a loop by knotting together of the ends of the sutures, and (b) the prosthetic ligament which is attached to the looped sutures in any convenient manner.

In the case of harvested tissue which comprises tendon material and boney material (plugs) attached at each end of the tendon material, the sutures are taken through holes formed in one of the bone plugs and then knotted to complete the formation of the attachment loop.

This known technique and attachment device is recognised as being a useful advance in the art of ligament implantation, and the present invention seeks to further improve this known device and technique, to gain further technical advantages which will facilitate the use by a surgeon (in carrying out assembly of an implantation system for a particular patient), and which also will provide improved manufacture and stocking of an attachment device for use in implantation systems.

OBJECTS AND BRIEF SUMMARY OF THE INVENTION

According to the invention there is provided an attachment device for use in an implantation system which includes a prosthetic ligament, in order to guide the ligament to a required position in a bone tunnel formed in a bone joint between two adjacent bones, and to anchor one end of the ligament, said device comprising:

an elongate guide element which is manipulatable between a pulling position in which its longitudinal axis extends generally parallel to the pulling direction and an anchoring position in which its longitudinal axis extends transversely of the pulling direction;

a connecting loop of flexible and implantable material which is connected, or connectable, at one end to the guide element and at its other end is connectable to one end of the prosthetic ligament to be implanted, said loop comprising a cohesive assembly of twisted filaments;

connecting apertures formed in the guide element which permit the loop to be connected thereto; and, connecting means provided on the guide element to permit pulling means to be connected to the element in order to pull the guide element, and trailing implantation system connected thereto, through the bone tunnels with the guide element orientated so that its longitudinal axis extends generally parallel to the pulling direction until the element emerges from the mouth at one end of one of the tunnels, whereby the guide element is manipulatable by the pulling means so as to overlie the mouth and thereby anchor one end of the implantation system.

The loop may be pre-formed, and then connected to the guide element.

Alternatively, the loop may be formed simultaneously, by twisting together of filaments of a bundle, and also with its connection to the connecting apertures in the guide element.

The connecting apertures in the guide element may take any suitable form, to permit easy connection of the connecting loop. In one preferred form, the connecting apertures comprise an adjacent pair of holes, with each hole having an entry slot which allows the loop to be easily assembled with the guide element by sliding of part of the loop into it. Each entry slot may be generally "funnel-shaped" to facilitate entry of the loop material into the aperture, but which will be more resistant to possible unintended withdrawal from the aperture.

The filament fibre bundle making up the loop may comprise a very loosely structured rope or hank type form, so that it forms a recognisable loop having two opposite return ends joining together two separate runs of the loop. This fibre bundle therefore can be easily assembled with the connection holes in the guide element, by sliding of a run of the bundle through the guide slots.

Alternatively, a fibre bundle may be "threaded" through an adjacent pair of holes (forming said connecting apertures) in the guide element, and with manipulation of the fibre bundle so as to form a continuous loop connected to the guide element. In this alterative arrangement, entry slots to the adjacent pair of holes are no longer required.

The assembly of the loop bundle can easily be carried out by the surgeon who is carrying out the ACL restructuring, and if the surgeon decides that the length of the connecting loop (for a particular patient) between the guide element and the adjacent end of the prosthetic ligament requires to be reduced, it is a simple matter to wrap the connecting loop more than one time around the connecting web in the guide element between the pair of adjacent holes.

This is a distinct advantage, both to the surgeon in carrying out the implantation, and also from the point of view of manufacture and stocking of a range of pre-formed loop sizes. This is of particular importance, because the length of the connecting loop will determine the precise positioning of the leading end of the ligament as it is being pulled into position, and precise positioning is technically important, since if the ligament end is drawn too high up into the bone tunnel, there may be an insufficient length of ligament trailing behind it, (or tension elements connected to it), to allow reliable fixation at the entry to the bone tunnel in the tibial component. Alternatively, if the leading end of the ligament is located too far down the bone tunnel in the femoral component, inadequate tissue ingrowth may arise, giving unreliable long term implantation of the ligament.

However, in some circumstances, it may be desirable to provide pre-assembled devices (guide element plus already attached connecting loop) and which can be assembled on a mass production basis. This obviates the need to "thread" the connecting loop material through the connecting apertures in the guide element, by the surgeon in the operating theatre.

This will be particularly applicable when one size of loop is appropriate, or adequate. The pulling means e.g. sutures also may form part of the pre-formed assembly, if required.

The invention also includes a novel method of carrying out implantation of a prosthetic ligament, using an attachment device as defined above, and optionally with one or more of the preferred aspects thereof.

BRIEF DESCRIPTION OF THE DRAWINGS

Preferred embodiments of the invention will now be described in detail, by way of example only, with reference to the accompanying drawings, in which.

DETAILED DESCRIPTION OF THE PREFERRED EMBODIMENT

Figure 1:
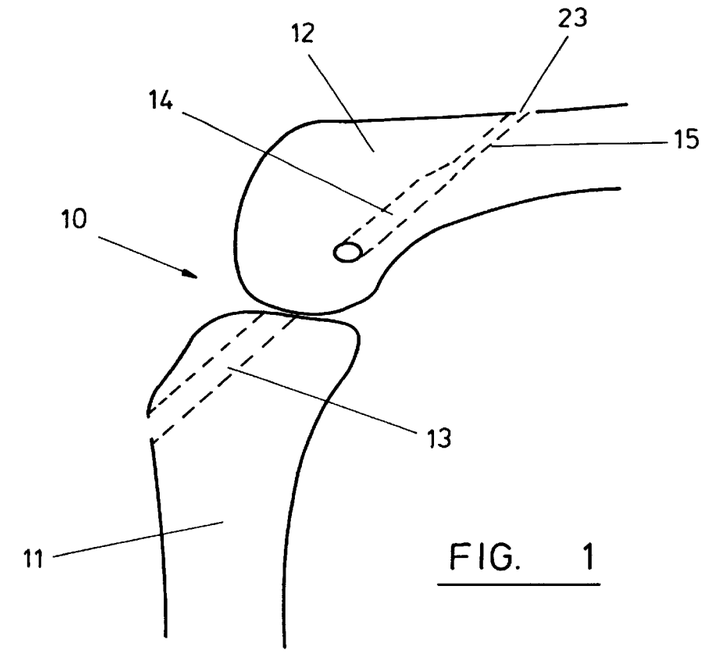
FIG. 1 is a schematic illustration of the femoral and tibial components of a knee joint, in which ACL reconstruction is to take place.

Referring first to FIG. 1 of the drawings, there is shown a typical type of bone joint with which the invention may be used, and which comprises a knee joint 10 which comprises tibial component 11 and femoral component 12. Enlarged bone tunnels 13 and 14 are drilled through the components 11 and 12, and in which a prosthetic ligament is to be implanted, but it will be noted that the bone tunnel 14 merges into a passage 15 of smaller diameter, the purpose of which will be explained in more detail below.

The described embodiment of the invention provides an attachment device for use in an implantation system which includes a prosthetic ligament, and which serves to guide the ligament to a required position i n a bone tunnel formed in a bone joint between two adjacent bones, and also serves to anchor the leading end of the ligament.

Figure 2:
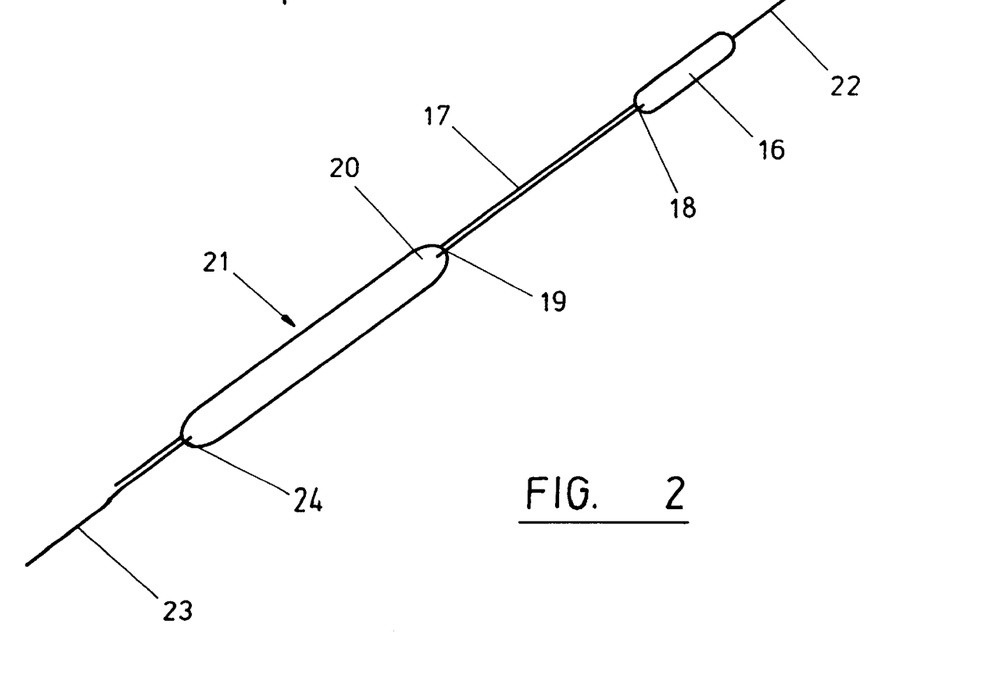
FIG. 2 is a schematic and enlarged view of an implantation system embodying the invention, and intended to be pulled through the bone tunnels formed in the knee joint components shown in FIG. 1, to implant a prosthetic ligament and anchor it therein.

An implantation system is shown schematically in FIG. 2, and comprises a guide element 16 which is generally elongate, having a major axis and a minor axis, and which is manipulatable between a pulling position in which its longitudinal axis or major axis extends generally parallel to the pulling direction (as shown in FIG. 2), and an anchoring position in which its longitudinal axis extends transversely of the pulling direction.

A pre-formed connecting loop 17 is connected at one end 18 to the guide element 16, and is connected at its opposite end 19 to a leading end 20 of a prosthetic ligament designated generally by reference 21. Prosthetic ligament 21 may be a woven synthetic material ligament, or may comprise autogenous tissue harvested from the patient.

The leading portion of the implantation system comprises pulling means 22, connected to the guide element 16, and the trailing end of the system comprises tensile elements 23 connected to the trailing end 24 of the ligament 21.

The implantation system is shown only schematically in FIG. 2, and the construction, and means of interconnecting the component parts of the system will be described in more detail below and also shown in more detail in FIGS. 3 to 6 of the drawings.

Figure 3:
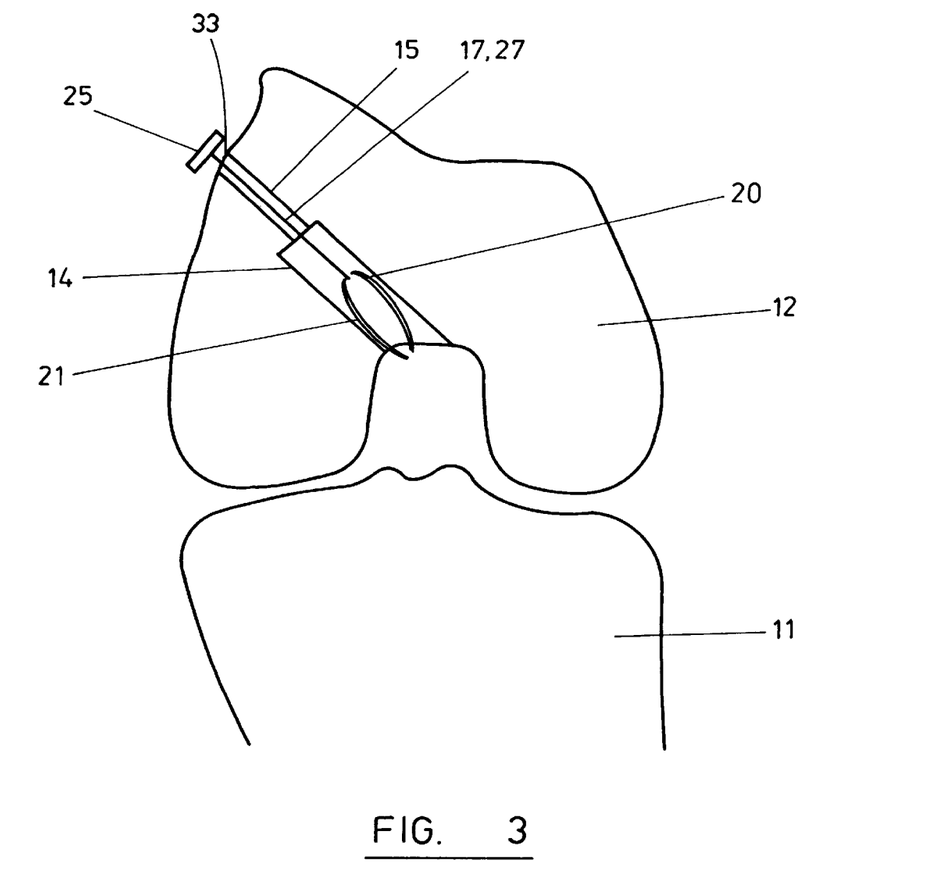
FIG. 3 is a schematic view, showing implantation of a prosthetic ligament.

FIG. 3 shows part of the implantation system anchored in position in the femoral component 12.

Figure 4:
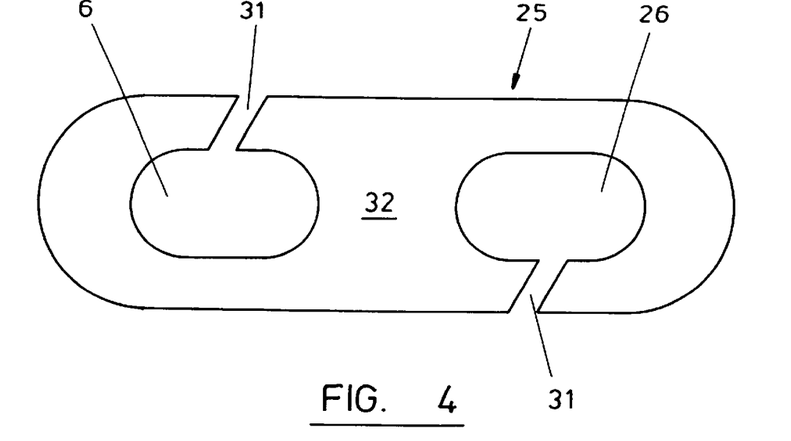
FIG. 4 is a plan view, to a considerably enlarged scale, of a guide element of an attachment device according to the invention.
Figure 5:
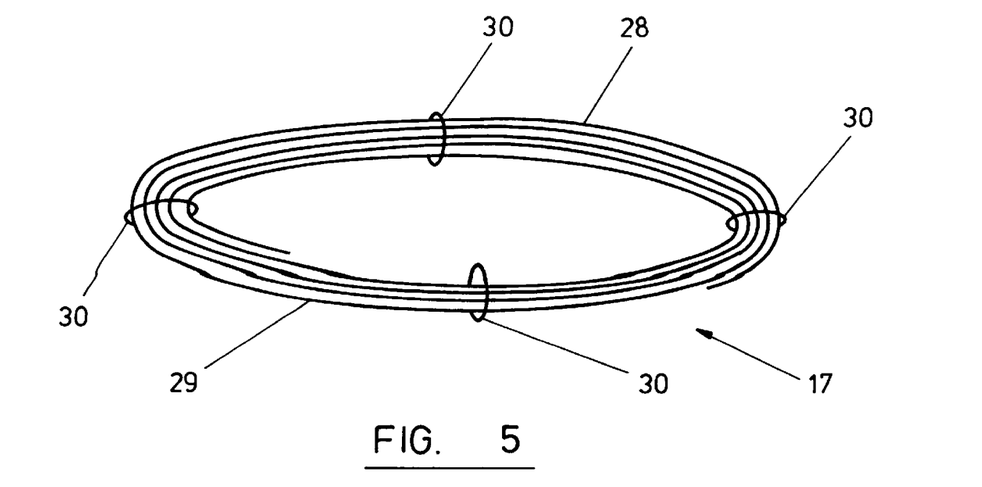
FIG. 5 is a plan view of a pre-formed connecting loop which can be connected to the guide element shown in FIG. 4, to form part of an implantation system.

The guide element is shown to a greatly enlarged scale in FIG. 4, and comprises a metal bar or strip, designated generally by reference 25. It has a pair of connecting apertures 26, and which permit the pre-formed loop, shown in FIG. 5, and designated generally by reference 27, to be connected to the guide element 25 in its already looped form. The loop 27 therefore can be produced by mass production techniques, and comprises a loosely structured fibre bundle or hank, comprising slightly twisted monofilamentary yarns. As shown in FIG. 5, the loop 27 is formed from a single yarn, formed into continuous loop, and in which the bundle is maintained in its shape, i.e. two opposed runs 28 and return ends 29 by means of simple ties 30.

The runs 28 and 29 of the loop 27 can readily be connected to the guide element 25 by sliding the runs through entrance slots 31 leading to the holes 26. The slots 31 are angled in such a way as to allow easy manipulation by the surgeon, who completes the assembly for a particular patient, and if the distance between the leading end 20 of the ligament 21 from tire guide element 16 is to be changed, it is a simple matter to achieve this, using a standard size of loop 27, by wrapping it one or more times around the web 32 of the element 25 between the holes 26.

Connection means are also provided on the guide element 25 (not shown) to permit pulling means 22 to be connected thereto, and in one preferred arrangement the connection means may actually be formed by the holes 26. However, alternative means may be provided, e.g. connection eyes or the like. The pulling means 22 can be operated to pull the guide elements 25 and the trailing implantation system connected thereto, through the bones tunnels 13 and 14, and the guide element 25 orientates itself so that its longitudinal axis extends parallel to the axes of the tunnels 13 and 14 and in the pulling direction, so that it presents minimum lateral projection from this axis. The metal bar forming the guide element 25 typically may have a length of 10 mm, a width of 3 mm, and a thickness of 1 mm. The final passage 15 in the femoral component 12 is therefore slightly larger in diameter than the transverse dimension of the guide element, thereby allowing the pulling means 22 to pull the guide element 16 (bar 25) through bone tunnel 14 and narrow passage 15, and then emerging from the mouth 33. FIG. 3 shows the bar 25, after it has been manipulated to a transversely extending position in which it overlies the mouth 33, and thereby provides anchorage for the leading end 20 of the ligament 21.

The pulling means 22 comprises a pair of pulling sutures, and conveniently each suture is connected to a respective hole 26, and these are pulled through the bone tunnels, and then one of these is used as the main pulling suture to pull the implantation system behind it until such time as the bar 25 emerges from the mouth 33. The other pulling suture can then be pulled in order to manipulate the bar 25 to take-up the anchoring position.

Figure 6:
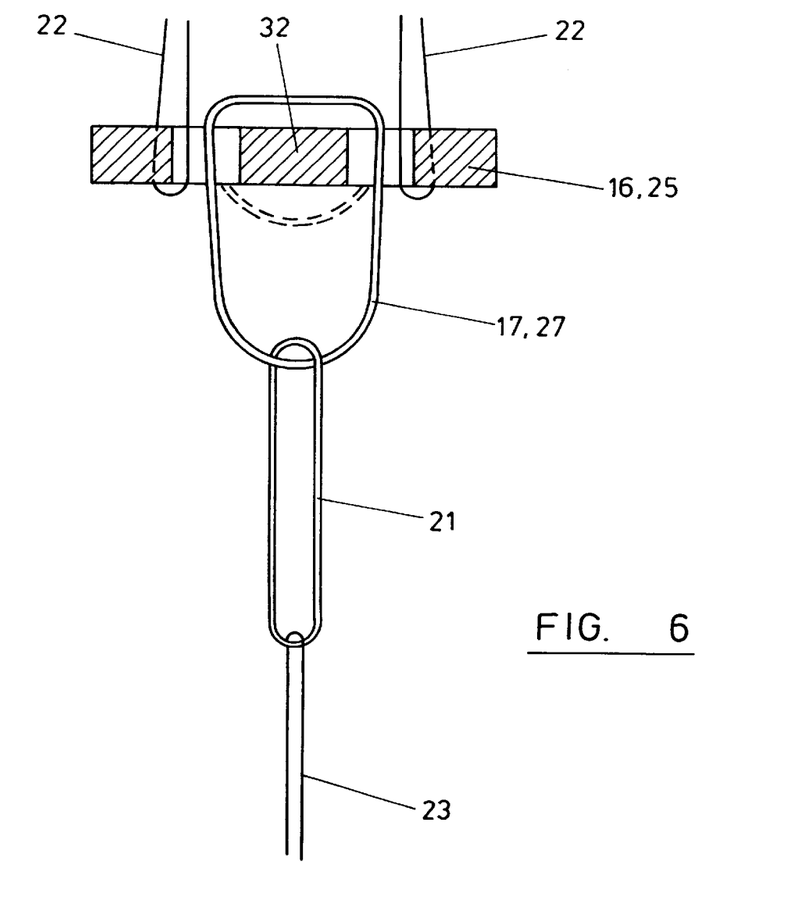
FIG. 6 is a schematic and greatly enlarged view of the implantation system, comprising the guide element of FIG. 4, the connecting loop of FIG. 5, an attached prosthetic ligament, and pulling means attached to the guide element to pull the entire implantation system through the bone tunnels for implantation.

FIG. 6 is an enlarged view of the implantation system, and showing the position taken-up by the bar 25 when in the anchoring position.

By providing the means whereby the effective length of the loop 27 can be changed, by wrapping turns more than once around the web 32, as shown by dotted lines in FIG. 6, a small number of different size loops 17 can be manufactured, and supplied to the surgeon, and who can cover a range of possibilities with each particular loop that he selects, to meet patient requirements. In this respect, having reference to FIG. 3, the distance a (the length of narrow passage 15) and the length of bone tunnel 14, represented by reference b, will vary from patient to patient, and it is desirable that the leading end 20 of the ligament 21 should be located about a minimum of 20 mm from the lower end of the tunnel 14, and the effective length of the loop 27 therefore can readily be adjusted accordingly. Manufacture only of a small range of standard loops can take place, and which can be adjusted to suit different patient requirements at the discretion of the surgeon, who can easily adjust the system to suit particular requirements.

The loop 27 is a fibre bundle or hank, comprising, in a typical case, 96 mono filaments very loosely twisted together to form a single yarn i.e. at about 48 turns per meter, and which is formed with overlapping looped portions which are held together in a loosely structured fibre bundle by ties 30, as shown in FIG. 5.

Figure 7:
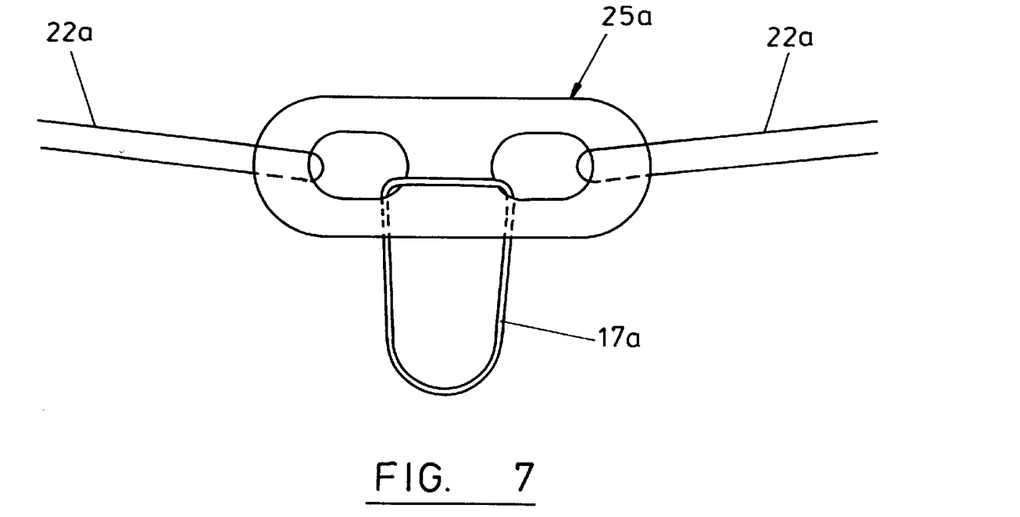
FIG. 7 is a schematic view of a pre-formed assembly according to the invention (guide element plus already attached connecting loop) ready for use by a surgeon.
Figure 8:
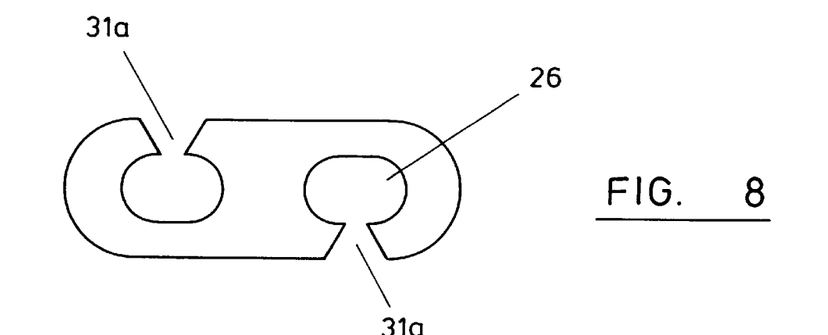
FIG. 8 is a schematic view of a modification of the guide element shown in FIG. 4.
Figure 9:
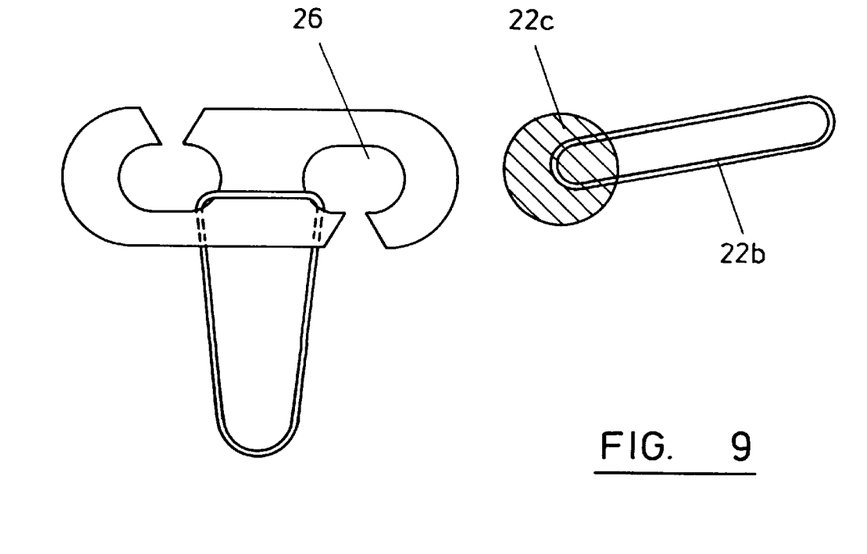
FIG. 9 is an exploded view of a modified pulling arrangement.

Various alternative embodiments are shown in FIGS. 7, 8 and 9, which will now be described.

FIG. 7 shows a schematic view of an already pre-formed assembly according to the invention, comprising guide element 25a plus already attached connecting loop 17a, ready for use by a surgeon. This can be assembled on a mass production basis, and obviates the need to "thread" the connecting loop material through the connecting apertures in the guide element, which will be carried out by the surgeon in the operating theatre in respect of the embodiment shown in FIG. 4.

FIG. 8 shows a modified arrangement of entry slot to the connecting apertures 26, in which funnel-shaped entry slots 31a facilitate entry of the loop material into the apertures 26, but which will be more resistant to possible unintended withdrawal from the apertures.

FIG. 9 shows a modified pulling arrangement, in which pulling sutures 22b may have a large knot or other enlargement 22c at one end, whereby upon introduction of the suture 22b into the aperture 26, followed by tightening, the knot or enlargement 22c overlies the aperture 26 and provides tensile restraint against pulling force applied to the suture 22b. One or preferably a pair of such modified pulling means may be provided.

Figure 10:
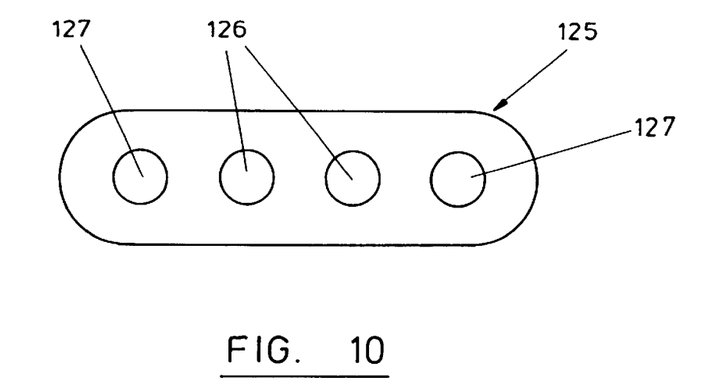
FIG. 10 is a schematic plan view of an alternative construction of guide element, in the form of a metal bar having four holes, comprising an outer pair for connection to two separate pulling means, and an inner pair to which a connecting loop can be coupled.
Figure 11:
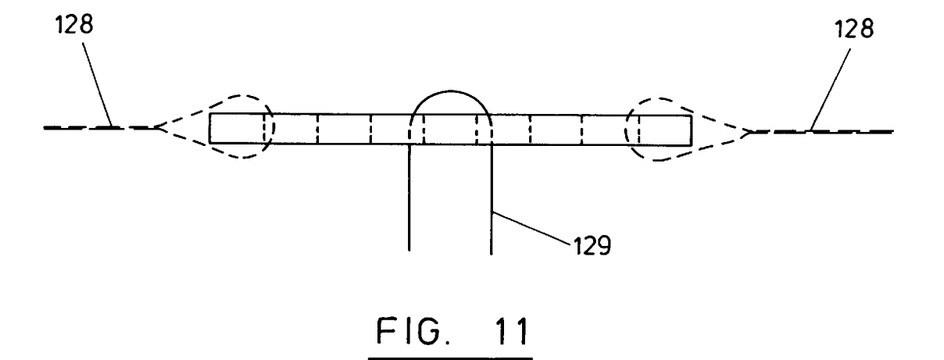
FIG. 11 is a schematic side view of the guide element shown in FIG. 10, and having pulling means connected to the outer pair of holes, and a connecting loop coupled with the inner pair of holes.

Referring now to FIGS. 10 and 11, this shows a further construction of guide element which may. be used in an embodiment of the invention. The guide element is designated generally by reference 125, and has an inner pair of holes 126 and an outer pair of holes 127. As shown in FIG. 11, pulling means 128 is attached to each of the outer holes 127, and which function in a generally similar manner to the pulling means 22 referred to earlier. FIG. 11 also shows part of a connecting loop 129, and which is connected to the central pair of apertures 126. Loop 129 can be a pre-formed loop, or may be formed by twisting together multi-filament yarns, which are formed simultaneously with the threading of the fibre bundle through the apertures 126. The loop 129 serves for attachment of a prosthetic ligament, as described earlier.

Figure 12:
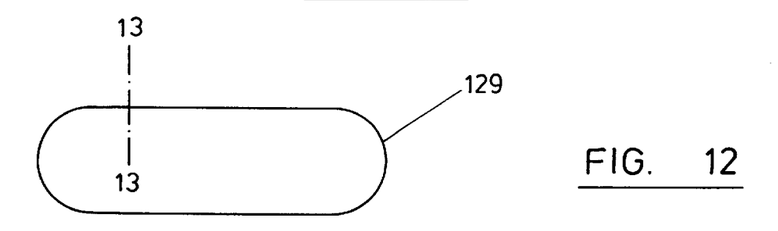
FIG. 12 is a plan view of a further arrangement of a pre-formed connecting loop which can be connected to the guide element shown in FIGS. 4 or 10.

One example of the way in which loop 129 can be formed will now be described with reference to FIGS. 12 and 13. A continuous loop 129 is formed, as shown in FIG. 12, and which is derived from twisting together of mono-filaments, eg 96 filaments, to form a single yarn, and in a relatively lightly twisted manner. The yarn is then formed into a number of looped portions e.g. twenty or forty "ends", which are simultaneously twisted together to form a cohesive looped bundle. However, by virtue of the "spinning" process involved, a cohesive looped structure is formed, which does not require additional means to maintain the integrity of the loop form, eg does not require the provision of separate ties 30 as described above with reference to FIG. 5. The twisting together of the filaments, and of the looped portions of the yarn is sufficient to form a cohesive structure, which maintains its looped form.

The looped bundle 129 is preferably formed simultaneously with the passage of the bundle components through the apertures 126. This may be achieved by any suitable spinning technique.

Figure 13:
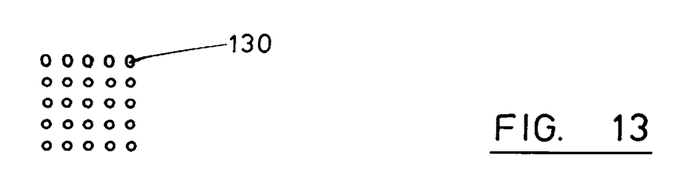
FIG. 13 is a cross section taken on the line 13—13 in FIG. 12, showing the twisted together filamental yarns making up the looped fibre bundle shown in FIG. 12.

The looped bundle 129 is derived from a single yarn formed from twisted-together mono filaments, of which one run is shown by reference numeral 130 in FIG. 13. The yarn is formed into a series of overlapping looped runs 130, e.g. twenty as shown in FIG. 13, and these runs are also twisted together to form a cohesive fibre bundle.

What is claimed is:

1. An attachment device for use with a prosthetic ligament, the attachment device comprising:
   (a) an elongate guide element extending between opposing ends and bounding a first connecting aperture and a spaced apart second connecting aperture, the first and second connecting apertures being separated by a web portion;
   (b) first and second lines connected at corresponding opposing ends of the guide element; and
   (c) a connecting loop comprised of flexible and implantable material, the connecting loop being looped through the first and second connecting apertures so as to be supported by the web portion, the connecting loop being configured for attachment to the prosthetic ligament, at least one of said first and second lines being configured to facilitate selective pulling of the guide element and prosthetic ligament through tunnels formed in the bone until said guide element exits one of said tunnels whereby said guide element is manipulated by said lines to overlie an opening of the tunnel, thereby anchoring said guide and ligament to the bone.

2. An attachment device as recited in claim 1, wherein the connecting loop is comprised of a plurality of twisted filaments.

3. An attachment device as recited in claim 1, wherein the connecting loop is comprised of an elongated coiled filament.

4. An attachment device as recited in claim 1, in which the connecting loop is formed from a single yarn comprised of twisted-together monofilaments, and in which the single yarn forms an assembly of looped portions which are twisted together to form a cohesive loop.

5. An attachment device as recited in claim 1, in which the connecting loop is formed from a single yarn comprised of twisted-together filaments, and in which the single yarn forms an assembly of looped portions maintained in looped form by ties wrapped around the assembled portions.

6. An attachment device as recited in claim 1, further comprising a first entry slot extending through the guide element and communicating with the first connecting aperture and a second entry slot extending through the guide element and communicating with the second connecting aperture.

7. An attachment device as recited in claim 6, wherein the guide element has a first side edge and an opposing second side edge each longitudinally extending between the opposing ends of the guide, the first and second entry slot each extending through the first side edge.

8. An attachment device as recited in claim 6, wherein the guide element has a first side edge and an opposing second side edge each longitudinally extending between the opposing ends of the guide element, the first entry slot extending through the first side edge and the second entry slot extending through the second side edge.

9. An attachment device as recited in claim 1, further comprising a hole positioned at each opposing end of the guide element, the first and second line each being feed through a corresponding hole for attachment to the guide element.

10. An attachment device as recited in claim 1, wherein the first and second line are each comprised of a suture material.

11. An attachment device to be used as a guide and an anchor for a prosthetic ligament, said attachment device comprising:
    an elongated guide element defining a longitudinal axis, said guide element capable of being manipulated between a pulling orientation where said longitudinal axis extends generally parallel to a pulling direction and an anchoring orientation that is generally transverse to the pulling direction;
    connecting apertures formed in said guide element;
    a connecting loop comprising a cohesive assembly of twisted filaments, said loop having one end attached to said connecting apertures and an opposite end attachable to the prosthetic ligament;
    pulling means connected to said guide element for pulling the guide element in said pulling orientation and prosthetic ligament through tunnels formed in the bone until said guide element exits one of said tunnels whereby said guide element is manipulated by said pulling means to overlie an opening of the tunnel thereby anchoring said guide and ligament to the bone.

12. An attachment device according to claim 11, in which the connecting apertures comprise an adjacent pair of holes having a web disposed therebetween, each hole having an entry slot which allows the connecting loop to be assembled with the guide element by sliding part of the connecting loop into each entry slot.

13. An attachment device according to claim 12, in which the connecting loop is preformed and then connected to the guide element.

14. An attachment device according to claim 12, in which each entry slot has a tapered configuration beginning from said apertures and widening outwardly.

15. An attachment device according to claim 11, wherein said connecting loop comprises an elongated piece of rope or hank having opposing ends, the elongated piece of rope or hank being looped into a continuous loop and secured in the continuous loop by ties.

16. An attachment device according to claim 15, wherein the connecting loop comprises the elongated piece of rope or hank being looped into at least two loops.

17. An attachment device according to claim 12, wherein the continuous loop is looped around the web extending between the holes of the connecting apertures so that the connecting loop passes through each of the holes at least twice.

18. An attachment device according to claim 11, wherein the elongated guide element has opposing ends, the pulling means comprising a suture connected to one of the opposing ends of the guide element.

19. An attachment device according to claim 18, wherein the suture is connected to one of the opposing ends of the guide element by looping through one of the connecting apertures.

20. An attachment device according to claim 11, in which the connecting loop is formed from a single yarn comprised of twisted-together monofilaments, and in which the single yarn forms an assembly of looped portions which are twisted together to form a cohesive loop.

21. An attachment device according to claim 11, in which the connecting loop is formed from a single yarn comprised of twisted-together filaments, and in which the single yarn forms an assembly of looped portions maintained in looped form by ties wrapped around the assembled portions.

* * * * *